(12) United States Patent
Pourcho

(10) Patent No.: US 6,705,333 B1
(45) Date of Patent: Mar. 16, 2004

(54) PERFORATED DENTAL APPLIANCE CASE

(76) Inventor: William S. Pourcho, 303 Gray Woods La., Lake Angelus, MI (US) 48326

( * ) Notice: Subject to any disclaimer, the term of this patent is extended or adjusted under 35 U.S.C. 154(b) by 0 days.

(21) Appl. No.: 09/384,621

(22) Filed: Aug. 27, 1999

(51) Int. Cl.⁷ .................................................. B08B 3/04
(52) U.S. Cl. ....................... 134/135; 134/199; 134/200; 134/201
(58) Field of Search ................................ 134/135, 199, 134/198, 200, 201, 182; 206/63.5; 422/300; 433/229

(56) References Cited

U.S. PATENT DOCUMENTS

| | | | |
|---|---|---|---|
| 2,163,862 A | | 6/1939 | Wing |
| 2,669,243 A | * | 2/1954 | Reynolds et al. ........... 134/199 |
| 3,009,468 A | * | 11/1961 | Eberle ......................... 134/199 |
| 3,098,496 A | * | 7/1963 | Milbourne ................... 134/199 |
| 3,732,973 A | | 5/1973 | Crawford |
| 3,894,551 A | * | 7/1975 | Stohlman |
| 3,904,058 A | * | 9/1975 | Rosentein |
| 4,054,220 A | * | 10/1977 | Roeentein |
| 4,721,124 A | * | 1/1988 | Tuerkheimer et al. |
| 4,724,855 A | | 2/1988 | Jackson et al. |
| 4,784,167 A | * | 11/1988 | Thomas et al. |
| 4,891,857 A | * | 1/1990 | Pinsonneault |
| 4,903,718 A | * | 2/1990 | Sullivan |
| 4,922,939 A | | 5/1990 | Adamczyk |
| 4,991,759 A | | 2/1991 | Scharf |
| 5,209,784 A | * | 5/1993 | Bellman |
| 5,275,185 A | | 1/1994 | Florjancic |
| 5,305,876 A | * | 4/1994 | Brigham |
| 5,314,543 A | | 5/1994 | Elkins et al. |
| 5,335,394 A | * | 8/1994 | Cunningham et al. |
| 5,421,353 A | * | 6/1995 | Jakubowski |
| RE35,034 E | | 9/1995 | Albert |
| 5,758,675 A | * | 6/1998 | Scheyer |
| 5,840,261 A | * | 11/1998 | Monch |
| 5,904,216 A | * | 5/1999 | Barlet |
| 6,217,933 B1 | * | 4/2001 | Edwards et al. |

FOREIGN PATENT DOCUMENTS

| | | | |
|---|---|---|---|
| FR | 2738479 | * | 3/1997 |
| FR | 2760350 | * | 9/1998 |
| JP | 10-244233 | * | 9/1998 |
| JP | 11-151256 | * | 6/1999 |

OTHER PUBLICATIONS

European Patent Office 465,285 6–1991.*

* cited by examiner

Primary Examiner—Frankie L. Stinson
(74) Attorney, Agent, or Firm—St.Onge Steward Johnston & Reens LLC

(57) ABSTRACT

A container receiving dental appliances includes a pair of top and bottom members which are relatively displaceable between open and close positions of the container. Each of the members is provided with a respective plurality of apertures, so that the top and bottom members form a compartment therebetween in the closed position of the container which is traversed by a plurality of liquid streams passing through the apertures during washing of dental appliances enclosed in the container.

15 Claims, 3 Drawing Sheets

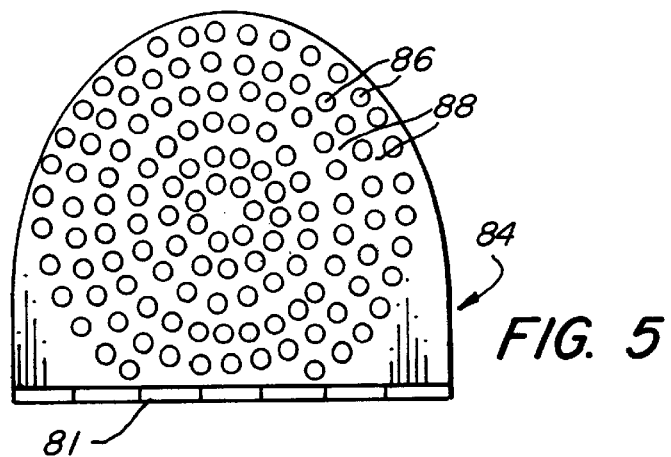
FIG. 5
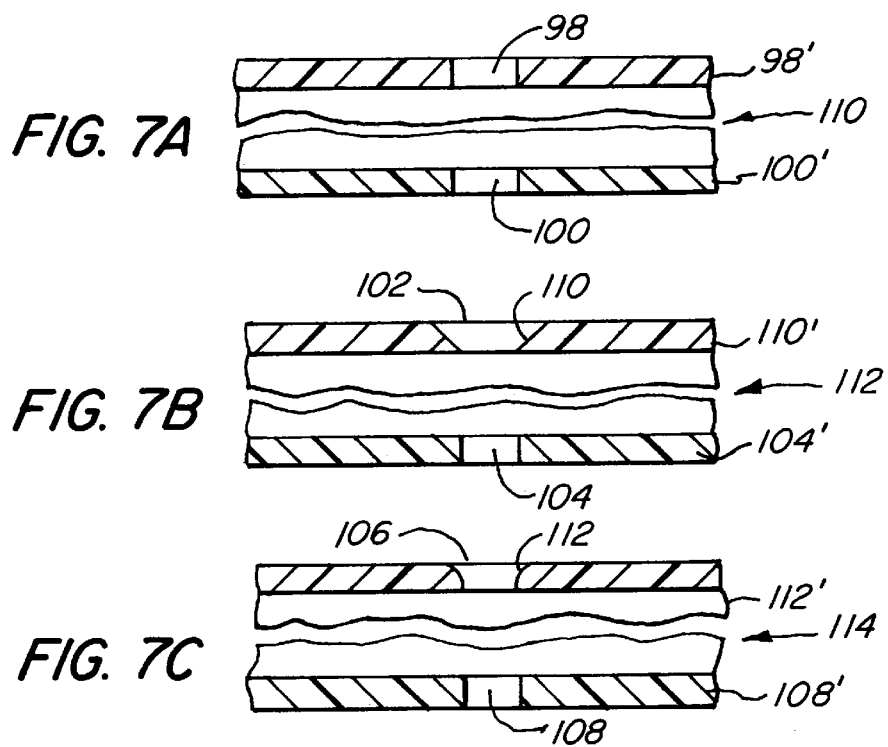
FIG. 7A
FIG. 7B
FIG. 7C
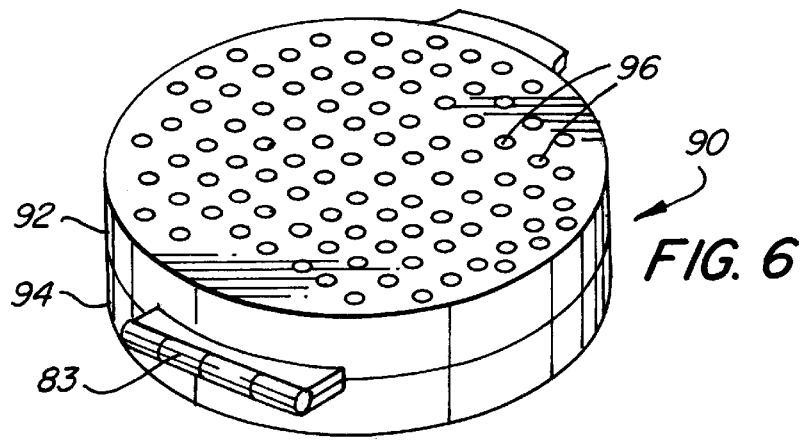
FIG. 6

PERFORATED DENTAL APPLIANCE CASE

FIELD OF THE INVENTION

This invention relates to containers for storing dental appliances. More particularly, the invention relates to dental containers for storing dental appliances enclosed therein which provide a cleaning process of these enclosed appliances during dishwashing.

BACKGROUND OF THE INVENTION

Plastic dental containers are used for either cleansing, storing or cleansing and storing dental appliances including retainers, dentures and other dental appliances. These appliances are usually cleansed by cleansing tablets, cleansing powders and rinsed by liquids which may enter an interior of these containers.

U.S. Pat. No. 5,275,185 discloses a retaining box receiving a plurality of dental appliances and pivotally connected with a lid. The retaining box has a plurality of partitions and slanted surfaces forming a whirling water jet of warm water which enters the box through a single filling funnel formed in the lid. The cleaning is carried out by a cleansing tablet placed in the box and entrained by the flow of water which, upon exceeding a predetermined level of filling of the box, exits the latter through a single outlet.

U.S. Pat. No. 2,163,862 discloses a stationary receptacle receiving a container for dental appliances which is closed by a perforated lid and has its bottom and peripheral wall perforated with a plurality of apertures opening into the receptacle. A dental appliance is placed on the bottom of the container and cleaned by a jet of water entering the container through the lid and exiting through the perforated bottom and wall in order to accumulate in the container.

U.S. Pat. No. 4,724,855 describes a denture washer having a washing container for housing the denture with a removable sealable lid. The container is formed with an outlet for exiting water which enters the container upon removing the lid.

U.S. Pat. Re. 35.034 discloses a disposable denture container having a pair of pivotally connected bottom and top members which are reliably closed to form a cleaning chamber that receives a cleansing tablet and water which is accumulated in the chamber for a period of time.

However, patients tend to complain how their dental appliances become stained, odoriferous, and nasty.

SUMMARY OF THE INVENTION

With one container in accordance with the invention an inexpensive easily manufactured dental appliance container is provided, which, when loaded in a dishwasher, provides an easy path for cleaning liquids leading to enclosed therein dental appliances.

This is achieved with one dental appliance container in accordance with the invention by providing a container with separable bottom and top members. Both top and bottom members are pierced by a plurality of apertures, so that a washing liquid can pass through the apertures and impact on an enclosed dental appliance from many different directions to effectively cleanse the appliance.

In accordance with one feature of the invention the top and bottom members are shaped to form an enclosure adapted to the shape of the dental appliance to be cleaned and provided with apertures distributed about the various surfaces of the members to supply cleaning liquid to the entire appliance while its movement within the enclosure is restricted.

According to another feature of the invention, both the top and bottom members are provided with apertures that are so located that critical parts of a dental appliance placed inside the container can be preferentially cleaned by liquid passing through the apertures into the container.

With another feature of the invention the apertures can be arranged in rows that are aligned with each other in a particular manner such as an alignment between aperture rows in top and bottom members or with aperture rows in circular arrangements or with randomly arranged apertures on both top and bottom members of the container.

Another aspect of the invention utilizes the apertures tending to increase the velocity of incoming jets of cleaning liquid. This is done as described in one form of the invention by shaping the walls of apertures in a particular manner such as narrowing apertures' cross-sections towards the interior of the container.

It is, therefore, an object of the invention to provide a dental container in which a dental appliance can be more effectively cleaned.

Still another object of the invention is to provide a dental container having a structure adapted to preferentially clean particular parts of a dental appliance inside the dental container.

DESCRIPTION OF THE DRAWINGS

The above and other objects, advantages and features of the invention will become more readily apparent, from the following detailed description of the invention, references being made to the following accompanying drawings, in which:

FIG. 5 is a top view of a clamshell container showing yet another aspect of the invention;

FIG. 6 is a perspective view of a clamshell container according to a further aspect of the invention:

FIG. 7A is a partial cross-sectional view of top and bottom members with apertures having cylindrical cross-sections;

FIG. 7B the same view but the aperture in the top member has a frustoconical shape while the aperture in the bottom member is cylindrical;

FIG. 7C is the same view but an aperture in the top member has a pair of inwardly curved-flank, the lower aperture is cylindrical.

DETAILED DESCRIPTION OF THE DRAWINGS

Figure 1:
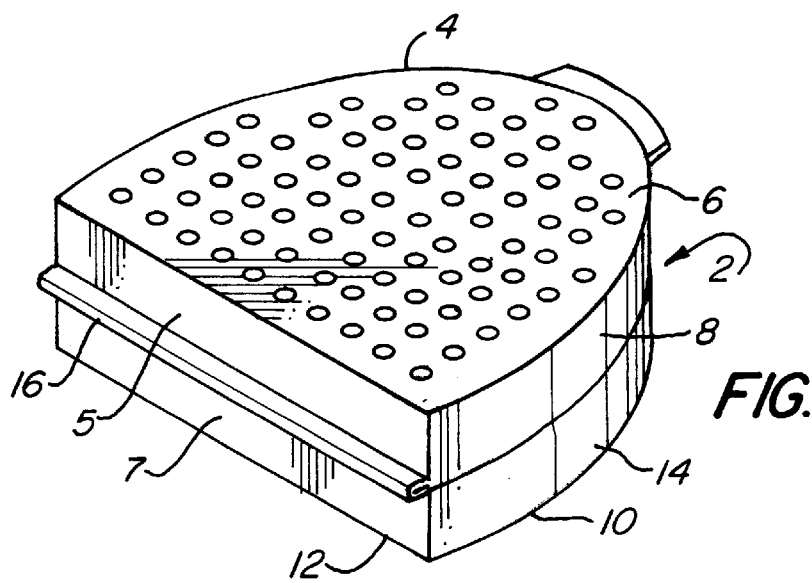
FIG. 1 is a perspective view of a clamshell container in accordance with the invention for cleansing and storing a dental appliance and is shown in a closed position.
Figure 2:
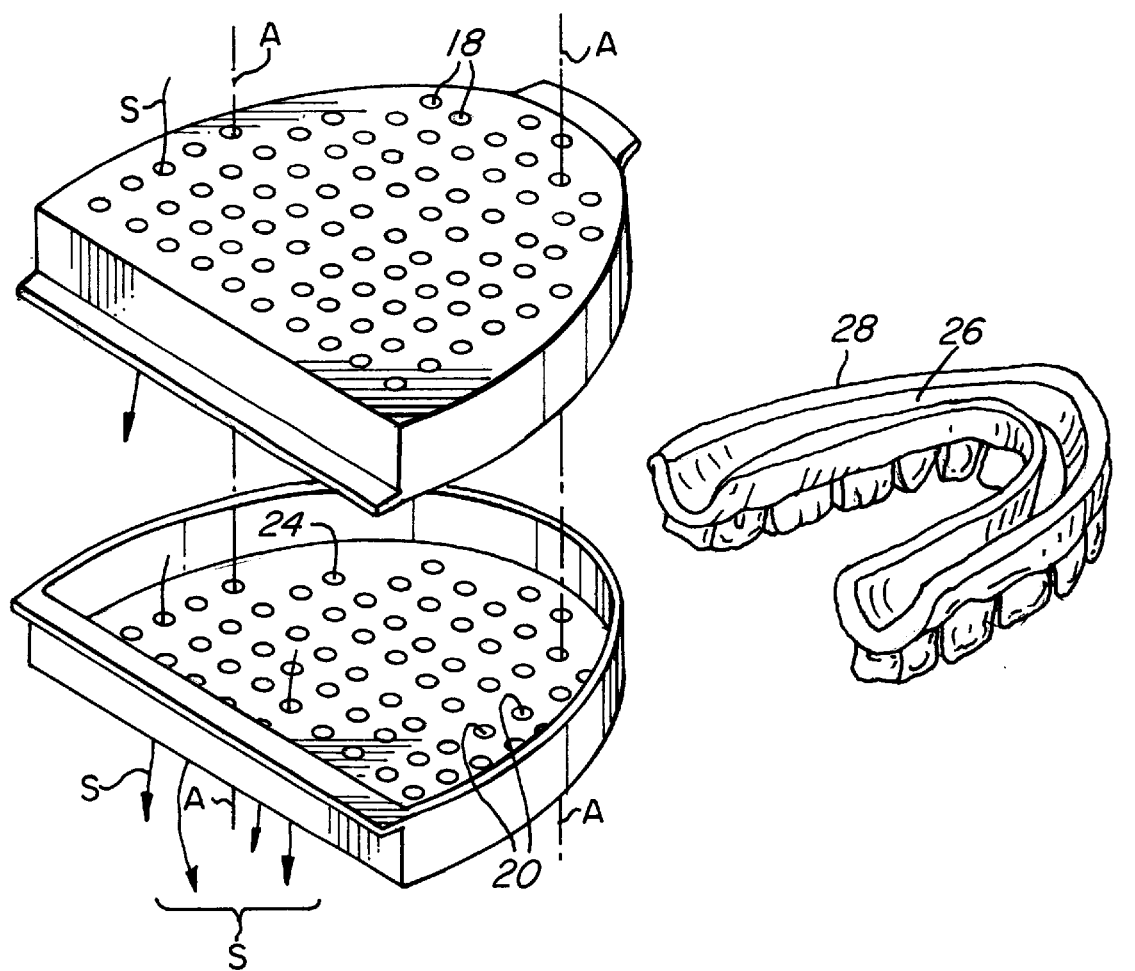
FIG. 2 is an exploded view of the container of FIG. 1 receiving prosthesis.

Referring to FIGS. 1 and 2, a clamshell container 2 in accordance with the invention includes a top member 4 formed with a top wall 6 which has a peripheral flange 8 extending transversely to the top wall 6. The container 2 further includes a bottom member 10 having a bottom wall 12 which is bounded by a peripheral flange 14 extending towards the flange 8 in order to make a mating contacttherewith in a closed position of the container 2. The top and bottom members 4, 10 are connected to each other by means of a hinge 16 with which the members 4, 10 can pivot between the closed position, as shown in FIG. 1 and an open position.

As shown in FIGS. 1 and 2, the top and bottom members 4, 10 have their walls 6, 12 pierced by a plurality of apertures 18, 20 respectively which are arranged in parallel rows 22, 24. As better seen in FIG. 2, the apertures 22 formed in the top member 4 are aligned with respective apertures 24 of the bottom member 10 along respective parallel axes A—A. In other words, the arrangement of the plurality of apertures 24 on the bottom member 10 is a mirror image of such arrangement of apertures 22 on the top member 4. The apertures 22, 24 are arranged to allow jets of a washing liquid to freely pass through them during washing of a denture enclosed in the container 2.

Particularly, as shown in FIG. 2 apertures 22, which are formed over substantially the entire wall 6 of the top member 4, form a plurality of washing liquid jets or streams S impacting upon practically the entire surface of a dental appliance 26 which may be, for example, a prosthesis 28. These streams S exit through apertures 20 of the bottom member 10.

Figure 3:
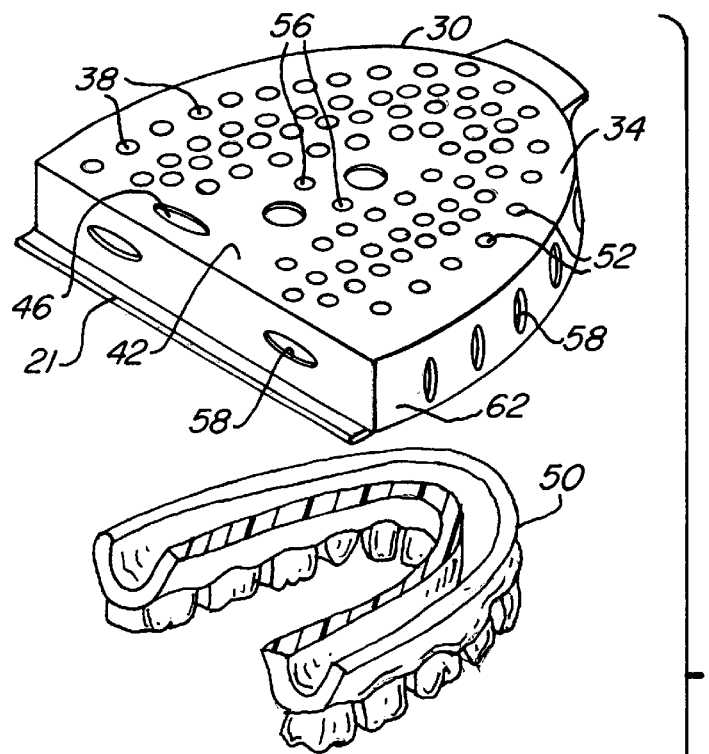
FIG. 3 an exploded view of a clamshell container according to another aspect of the invention.
Figure 3:
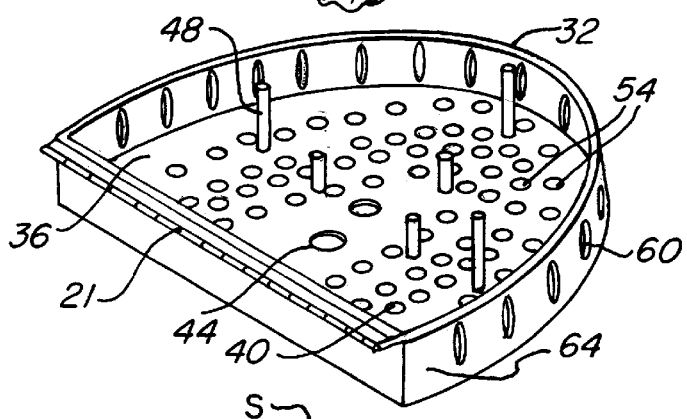

FIG. 3 shows another feature of the clamshell container according to the invention which includes a top member 30 and a bottom member 32. Each of wails 34 and 36 of the top and bottom members has a plurality of apertures 38 and 40 respectively arranged in a plurality of rows 52, 54 that substantially conform with a shape of a prosthesis 50. As is illustrated here, this shape has a horseshoe contour, but, of course, other contours of dentures enclosed in the container may be easily conceived.

A pattern of rows 54 of apertures formed at the bottom member's wall 36 may be completely different from the one of the top member's wall 34. As shown here, a few apertures 56 are randomly arranged. However, it is possible to have the entire plurality of apertures arranged randomly at the bottom member.

Further, apertures of each of the members 30, 32 may be differently sized. For example, apertures 42 of the top member 30 are larger than apertures 38, whereas apertures 44 of the bottom member 32 are larger than apertures 40.

According to another feature of the invention, apertures may have different shapes. For example, apertures 46 of the top member 30 have generally ellipsoidal shapes, whereas a majority of the apertures 38 is circular. Apertures formed in both top and bottom members 30, 32, of course, are not limited to the shapes described above.

Also, both the top and bottom members 30, 32 may have regions which are characterized by a relatively high concentration of these apertures if compared with other regions. Usually, these, regions are strategically selected to supply additional streams of a cleaning liquid to critical areas of a dental appliance which are difficult to clean.

Another feature of this invention includes a plurality of apertures 58, 60 which are formed in flanges 62, 64 of the top and bottom members 30, 32 respectively. Dental containers are likely to be washed together in a dishwasher whether in a hospital or in a dental office. As a result, these containers may be randomly loaded in the dishwasher thereby blocking at least some of the apertures formed in the walls 34, 36 of the top and bottom members of individual containers. To overcome this problem, peripheral flanges 62,64 have apertures 58, 60 respectively that can provide access of a washing liquid into an interior of the container even if it has been placed in a dishwasher on the flanges 62, 64. These apertures 58, 60 may be either identical to or different from the apertures formed in the top and bottom members and may also have different shapes and arrangements.

The bottom member 32 has pins 48 which may be formed unitarily with its wall 36 and receive a prosthesis 50 in a predetermined position. Similar to variously sized and shaped arrangements of the apertures, a means for positioning the prosthesis 50 is not limited to pins and may include other formations placing the prosthesis in desirable positions.

Figure 4:
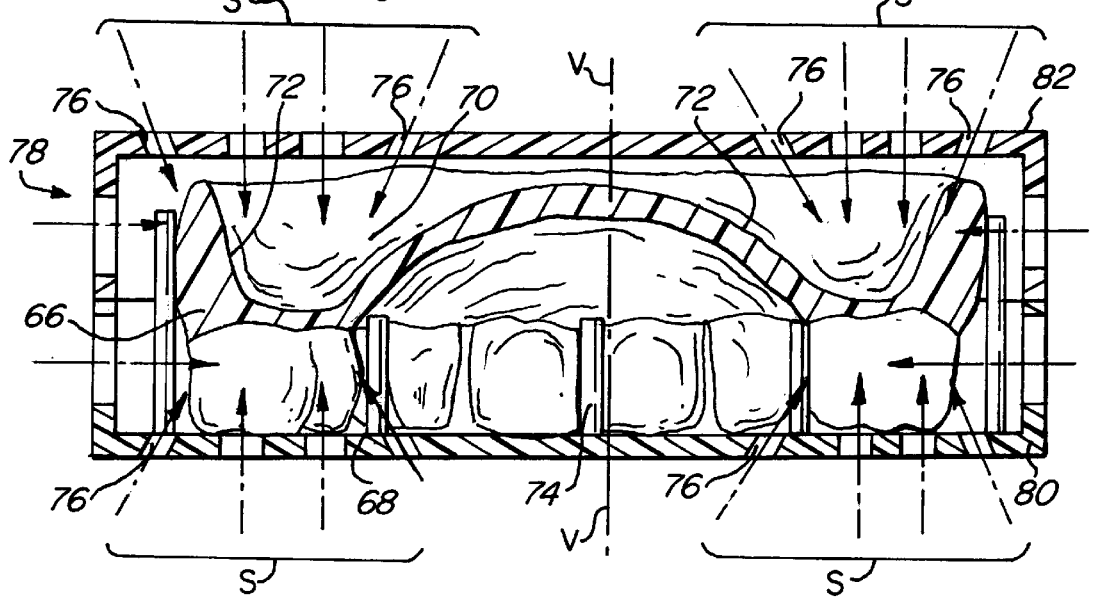
FIG. 4 is a cross-sectional view of a clamshell container according to still another aspect of the invention.

According to another feature of the invention, some of the apertures 76 may have its inner peripheral walls inclined to a vertical V—V, as is shown in FIG. 4, in order to direct liquid streams S to particular "critical" areas of a prosthesis 66 enclosed in a container 78. These "critical" areas may be less accessible for the liquid jets S than the other areas are. An example of such inconvenient areas may be smooth slopes 72 of troughs 70. Still another "critical" areas, for example, interstices 68 formed between adjacent teeth of the prosthesis 66, accumulate more impurities than other areas do during use of this prosthesis. Aligning these "critical" areas with specifically recessed apertures 76 enables liquid cleaning streams S to pass through these inclined apertures and to impact substantially directly onto the critical parts of the prosthesis 66 for preferential cleaning.

A positioning means 74 for placing the prosthesis 66 in the container 78 so that the apertures 76 can be aligned with critical areas are formed on a bottom member 80. However it is possible to have such means on a top member 82 as well. Because certain types of dishwasher machines have a delivery system providing water supply from different directions, the liquid streams S are shown here to enter the container 78 through both the top and bottom members 82, 80.

FIG. 5 illustrates another feature of a container 84 according to the invention which has apertures 86 forming a plurality of concentric rows 88 which are uniformly radially spaced apart from one another.

FIG. 6 illustrates a clamshell container 90 including top and bottom members 92, 94, each of which has a circular shape and is formed with a plurality of apertures according to the invention.

FIG. 7A illustrates apertures 98, 100 formed in top and bottom members 98', 100' respectively. each of which has a cylindrical cross-section. Such structure provides a substantially uniform flow of a washing liquid traversing a container 110 which has a dental appliance enclosed therein.

FIG. 7B shows the top member 110' provided with an aperture 102 which has a frustoconical peripheral wall 110 narrowing towards a bottom member 104'. This frustoconical cross-section may cause an acceleration of a flow of water impacting a denture enclosed therein. The bottom member 104' has an aperture 104 with a cylindrical cross section.

FIG. 7C illustrates still another cross section of an aperture 106 which is formed in a top member 112' of a container 114 and whose peripheral wall 112 is radially inwardly curved. A bottom member 108' has a cylindrical aperture 108.

Although FIGS. 7B–7C show particularly shaped apertures 102, 108 which are formed in the top members 110' and 108' respectively, it should be understood that the bottom members 112' and 108' can be formed with similarly shaped apertures.

The hinges 16 and 21, which may be flexible members, pivotally connect the top and bottom members of the clamshell container, as is shown in FIGS. 1–3. The entire dental container 2 including the top and bottom members and the hinge may be molded as a unit from various known synthetic plastic materials by well-known molding technology. Preferably, the hinge 16 may run for a substantial length along back segments 5, 7 of the peripheral flanges 8, 14 respectively. Embodiments illustrated in FIGS. 5 and 6 have top and bottom members including tubular receiving elements 81 and 83 which are traversed by a connecting pin.

It is understood that any combination of differently shaped and differently sized apertures can be grouped together on the same container. However, the apertures' arrangements and shapes should enable effective access for the washing liquid to the dental appliances enclosed in the dental container according to the invention.

In view of the above, the present invention may be embodied in other specific forms without departing from the scope of the invention as recited in the appended claims.

What is claimed is:

1. A clamshell container for dental appliances, comprising:

first and second members hingedly connected to one another and displaceable with respect to each other between open and closed positions of the container, said first and second members having top and bottom surfaces respectively and being superimposed with each other in said closed position of the container to define a compartment therebetween to receive a dental appliance to be cleaned, and a plurality of apertures formed substantially over the entire top and bottom surfaces of said first and second members respectively, said apertures enabling a plurality of jets of a washing liquid to enter said compartment through the apertures of at least one of said first and second members and to exit said compartment through the apertures of the other member;

each of said top and bottom surfaces having a respective peripheral flange ex-tending transversely thereto; and wherein each of said peripheral flanges has at least one aperture.

2. The container defined in claim 1 wherein each of said top and bottom surfaces has a respective peripheral flange extending transversely thereto, said first and second members being pivotally connected to one another.

3. The container defined in claim 1 wherein an arrangement of the apertures in said first member is a mirror image of an arrangement of the apertures formed in said second member.

4. The container defined in claim 1 wherein at least one of the top and bottom second surfaces has the apertures arranged in at least one row thereof.

5. The container defined in claim 4 wherein the apertures are distributed in another row of apertures parallel to said one row.

6. The container defined in claim 1 wherein at least one of the top and bottom surfaces has the plurality of apertures forming at least one circle.

7. The container defined in claim 6 wherein the apertures are distributed in another circle concentric with the said one circle and spaced radially therefrom.

8. The container defined in claim 1 wherein at least one of said first and second members has uniformly sized apertures.

9. The container defined in claim 1 wherein at least one of the first and second members has differently sized apertures.

10. The container defined in claim 1 wherein the apertures of each of said first and second members are randomly distributed over the top and bottom surfaces respectively.

11. The container defined in claim 1 wherein each of said apertures is cylindrical.

12. The container defined in claim 1 wherein each of said apertures of at least one of said first and second members has a frustoconical cross-section.

13. The container defined in claim 1 wherein each of said apertures of at least one of said first and second members has a cross-section defined by inwardly curved flanks.

14. The container defined in claim 1 wherein at least one of said top and bottom members has at least one region formed with a concentration of said apertures higher than in other regions of said members.

15. A clamshell container for storing a dental appliance having critical parts which tend to accumulate impurities during the use of said dental appliance, said clamshell container comprising:

first and second members hingedly connected to one another and displaceable with respect to each other between open and closed positions of the container, said first and second members having top and bottom surfaces respectively and being superimposed with each other in said closed position of the container to define a compartment therebetween receiving a dental appliance in a predetermined position in which the dental appliance extends in a plane, and a plurality of apertures formed in said top and bottom surfaces of said first and second members respectively, at least some of said apertures being centered on respective axes which extend towards said plane of the dental appliance at acute angles, so that said some apertures are aligned with the critical parts of the dental appliance to enable liquid cleaning streams to pass therethrough and,to impact onto the critical parts of the dental appliance for preferential cleaning in said closed position; and a positioner formed on at least one of said top and bottom surfaces of said first and second members for placing the dental appliance in said predetermined position in which said some apertures are aligned with the critical areas of the dental appliance.

\* \* \* \* \*